(12) United States Patent
Danielson

(10) Patent No.: US 6,367,970 B1
(45) Date of Patent: Apr. 9, 2002

(54) RAPID RESPONSE H-Q-T SENSOR

(75) Inventor: Arnold O. Danielson, Inyokern, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/332,248

(22) Filed: Jun. 7, 1999

(51) Int. Cl.[7] .............................. G01N 25/20; G01K 7/06
(52) U.S. Cl. ............................ 374/43; 374/29; 374/179
(58) Field of Search ........................ 374/29, 43, 179, 374/31, 44; 338/22 R

(56) References Cited

U.S. PATENT DOCUMENTS

| | | | | |
|---|---|---|---|---|
| 3,767,470 A | * | 10/1973 | Hines | 136/225 |
| 4,542,650 A | * | 9/1985 | Renken et al. | 73/204 |
| 4,722,609 A | * | 2/1988 | Epstein et al. | 374/30 |
| 4,779,994 A | | 10/1988 | Diller et al. | 374/29 |
| 4,812,050 A | * | 3/1989 | Epstein et al. | 374/1 |
| 5,237,523 A | * | 8/1993 | Bonne et al. | 374/571.03 |
| 5,273,359 A | * | 12/1993 | Noel | 374/29 |
| 5,314,247 A | * | 5/1994 | Liebert et al. | 374/29 |
| 5,379,718 A | | 1/1995 | Onishi | 117/88 |
| 5,765,075 A | | 6/1998 | Yamamoto | 399/69 |
| 5,798,684 A | | 8/1998 | Endo et al. | 338/22 R |
| 5,990,412 A | * | 11/1999 | Terrell | 136/225 |
| 6,106,149 A | * | 8/2000 | Smith | 374/31 |

OTHER PUBLICATIONS

High Temperature Heat Flux Measurements, by J.M. Hager and L.W. Langley of Vatell Corporation of Christianburg, Virginia, and S. Onishi and T.E. Diller at the 29th Aerospace Sciences Meeting, Jan. 7–10, 1991 in Reno, Nevada.

* cited by examiner

Primary Examiner—Diego Gutierrez
Assistant Examiner—Gail Verbitsky
(74) Attorney, Agent, or Firm—Earl Baugher, Jr.; Anthony J. Serventi

(57) ABSTRACT

Provided in a compact system is a rapid response h-q-T sensor assembly, with associated processor and holding device, for measuring temperature, T, and heat flux, q, in a severe operating environment. From measured temperatures, T, and heat flux, q, a stagnation point recovery temperature, $T_r$, and a heat transfer coefficient, h, may be calculated using approximation algorithms loaded in the processor. The system approximates the ideal conditions in which $T_r$ is derived from measuring a high temperature, i.e., a zero heat flux path to ground, i.e., $q=0$, $r=\infty$ and a lower wall temperature measured along an infinite heat flux path, i.e, $q=\infty$, $r=0$. Although ideal conditions are not able to be duplicated, appropriate positioning of heat flux indicators and temperature indicators in the surface of a thin film on the q-h-T sensor assembly, while allowing for very short duration sampling in a hostile environment, permits a viable approximation. Using a pair of algorithms, the measured values of temperature, T, and heat flux, q, and calibrating a value of thermal resistance, data are processed in situ to yield derived values for the worst case heat transfer coefficient, h, and the stagnation recovery temperature, $T_r$.

39 Claims, 5 Drawing Sheets

RAPID RESPONSE H-Q-T SENSOR

STATEMENT REGARDING FEDERALLY SPONSORED RESEARCH AND DEVELOPMENT

The invention described herein may be manufactured and used by or for the government of the United States of America for governmental purposes without the payment of any royalties thereon or therefor.

BACKGROUND

1. Field of the Invention

The present invention relates to a rapid response h-q-T sensor. More particularly, two sensors are designed to simultaneously measure heat flux (q) and surface temperature (T) on parallel paths, thereby generating data that enables calculation of the heat transfer coefficient (h) and recovery temperature ($T_r$). Most particularly, the present invention uses thin film sensor technology to measure the upper-bound, i.e., uncooled boundary layer, stagnation-point heat transfer condition.

2. Brief Description of the Related Art

Thin film heat flux and temperature sensors have been developed by Vatell Inc. of Christiansburg, Vir. See U.S. Pat. No. 4,779,994, issued to Diller et al. Such sensors include a rapid response device suited to capture rocket plume conditions such as the HFM-1 (Heat Flux Microsensor), described in High Temperature Heat Flux Measurements, by J. M. Hager and L. W. Langley of Vatell Corporation of Christiansburg, Vir., and S. Onishi and T. E. Diller at the 29$^{th}$ Aerospace Sciences Meeting, Jan. 7–10, 1991 in Reno, Nev. The HFM-1 measures heat flux (q) and wall surface temperature ($T_{wall}$), producing a voltage out of the sensor thermopile array that is proportional to heat flux (q), with the voltage having a polarity indicating the direction of the heat flow. However, the HFM-1 design lacks the ability to establish values for the heat transfer coefficient (h) and the recovery temperature ($T_r$) that are useful in modeling severe thermal (e.g., rocket plume) environments.

Several patents have disclosed many aspects of sensor thin film technology, including U.S. Pat. No. 4,779,994 (Diller et al.), U.S. Pat. No. 5,379,718 (Onishi), U.S. Pat. No. 5,765,075 (Yamamoto), and U.S. Pat. No. 5,798,684 (Endo et al.), the disclosures of which are herein incorporated by reference. However, these patents do not address the methods of measurement and the means of calculation of the heat transfer coefficient (h) and the recovery temperature ($T_r$) as taught by the present invention.

The heat transfer coefficient (h) is a widely used parameter that provides a measure of combined radiation, convection, and conduction heat transfer modes for the thermal energy generated from a source of heat energy. The recovery temperature ($T_r$) provides a measure of peak temperature in a flowing mass efflux and offers a means to characterize the total energy within the flow stream. This is particularly important to know for supersonic applications in which aerodynamic heating becomes an important design driver.

SUMMARY OF THE INVENTION

It is an object of the present invention to provide a thin film sensor assembly that has a fast response and is thereby usable in severe thermal environments.

It is further an object of the present invention to provide a thin film sensor assembly that provides the data necessary to determine the heat transfer coefficient (h) and the recovery temperature ($T_r$) condition at a point in the measured mass efflux.

These and other objects are accomplished by the present invention which includes a thin film sensor comprising at least a first thin film, a first thin film heat flux indicator and temperature indicator integral to the first thin film structure mounted on a first substrate and capable of indicating a first temperature and a first heat flux into the front surface, and a second temperature sensor. Preferably, the second temperature sensor provides a temperature measurement at a different point on the front surface of the first thin film on the first substrate. In an alternative embodiment, the second temperature sensor may be integral to a second thin film assembly mounted on a second substrate electrically and thermally isolated from the first thin film assembly. In either embodiment, the thermal resistance between the second temperature sensor and a reference is much greater than that of the thermal resistance between the first temperature sensor and a reference. The present invention further includes a method for determining a heat transfer coefficient, h, comprising the steps of providing a thin film sensor assembly comprising at least a first thin film, a first thin film heat flux indicator and temperature indicator integral to the first thin film structure mounted on a first substrate for indicating a temperature and a heat flux into the front surface, and, a second thin film temperature indicator that provides a temperature measurement at a different point on the front surface of the first thin film on the first substrate in which the thermal resistance between the second temperature sensor and a reference is much less than that of the thermal resistance between the first temperature indicator, the first heat flux indicator, and a reference then, the h-q-T sensor assembly 10 is exposed to a severe environment.

DETAILED DESCRIPTION

The present invention is a rapid response h-q-T sensor assembly that simultaneously measures heat flux (q) and surface (wall) temperature ($T_{wall}$) using thin film technology. It is used for the subsequent calculation of heat transfer coefficient (h) and recovery temperature ($T_r$), and is most often applied to determine the stagnation point condition. The determination of these measured and calculated values is necessary to enable the cost-effective design and construction of engineered components that are normally exposed to excessive heat and/or severe environmental conditions. Example applications that include excessive heat and severe thermal environments include exposure to rocket plumes, conditions in burning buildings, bomb blasts, volcano lava flows and other such environments having temperatures in excess of 1000° R. Rocket plumes may possess particulate $Al_2O_3$ matter in concentrations up to 21%, and stagnation-point recovery temperatures in excess of 6000° F. Particulate erosion tends to both melt and erode objects placed in this rocket motor exhaust flow, especially when exposure is greater than ½ second in duration. Limited exposure remains important, even for highly refractory materials, such as tungsten-zirconium-molybdenum alloy (TZM), copper-infiltrated tungsten and molybdenum.

Figure 2A:
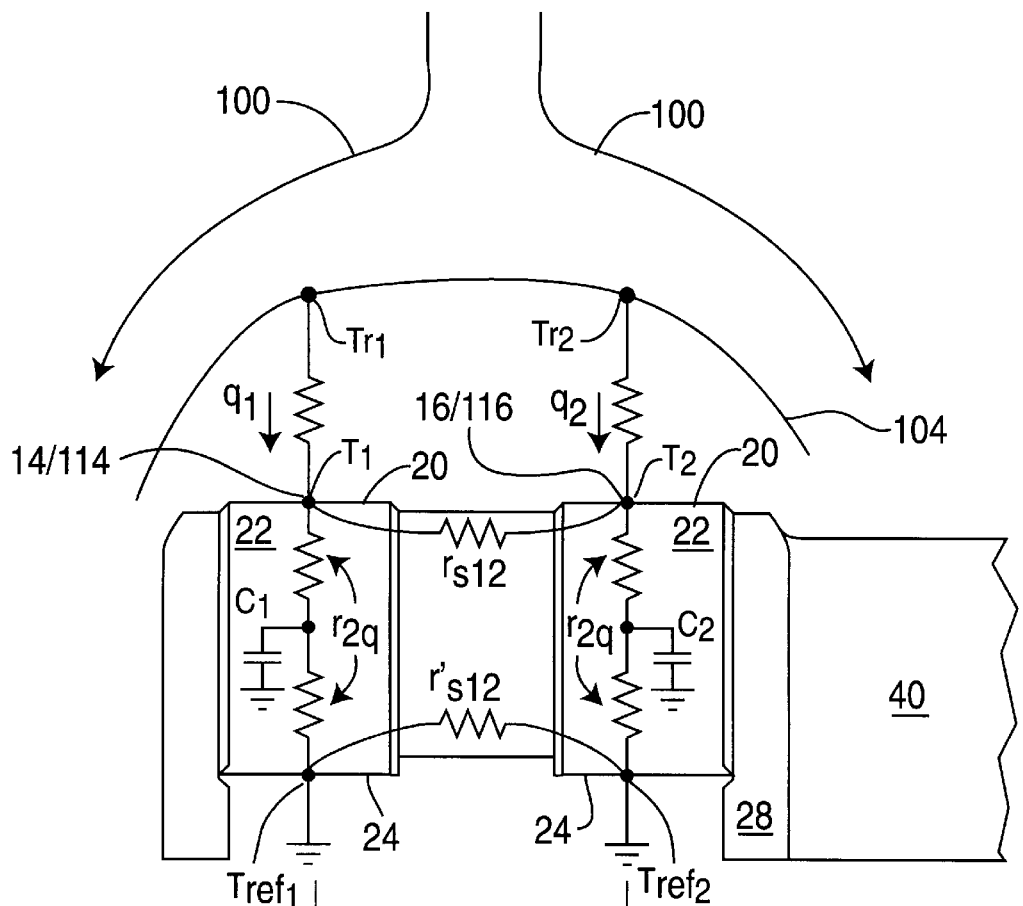
FIG. 2A shows the equivalent electrical circuit of a preferred embodiment of the rapid response thin film sensor components only of the present invention, highlighting those elements that are required measurands and those that are derived values.
Figure 2B:
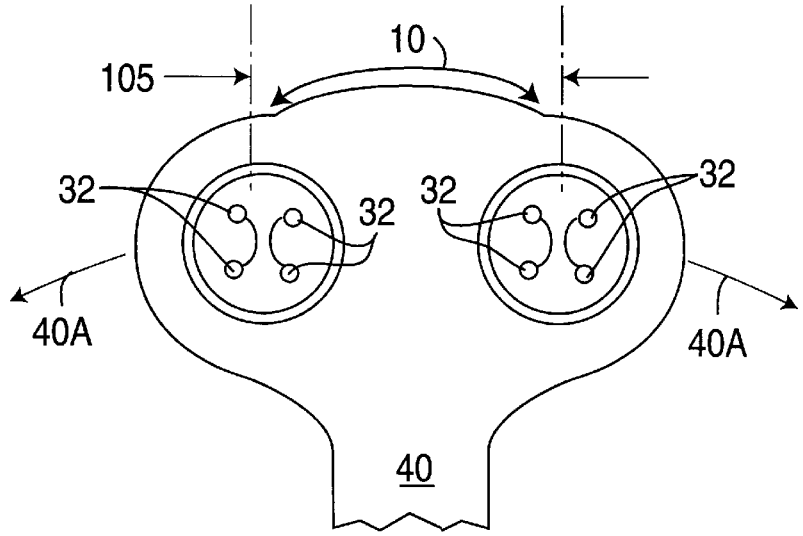
FIG. 2B illustrates the physical appearance of the h-q-T sensor assembly 10 shown in FIG. 2A.

As seen in FIG. 2B, the h-q-T sensor assembly 10 of the present invention relies on a specific arrangement of fast response thin film sensing elements 14, 16 for measuring temperatures $T_1$ and $T_2$ and heat flux indicator $q_1$ 114 to measure heat flux $q_1$ 17 within high heat, corrosive and/or severe environmental conditions. The use of thin film technology in the thin film sensor 12 portion of the h-q-T sensor assembly 10 provides a sub-millisecond determination of heat flux $q_1$ 17 via heat flux indicator 114, and surface temperature $T_1$ via a first temperature indicator 14 and $T_2$ via a second temperature indicator 16, and by use of the inventive method, the calculated heat transfer coefficient (h) and stagnation recovery temperature ($T_r$) for rocket plumes and other similar environments. As such, the thin film sensor assembly 10 increases the accuracy of determining the total energy released during combustion as measured in experimental energetic mixes. Measurements of $q_1$ 17, $T_1$, and $T_2$, and the calculation of h and $T_r$ provide a better understanding of a given operational heating environment, aiding in the design of component parts that may be exposed to the heat, e.g., nozzles, jet vanes, turbine blades, wing leading edges, and/or probes.

Figure 1:
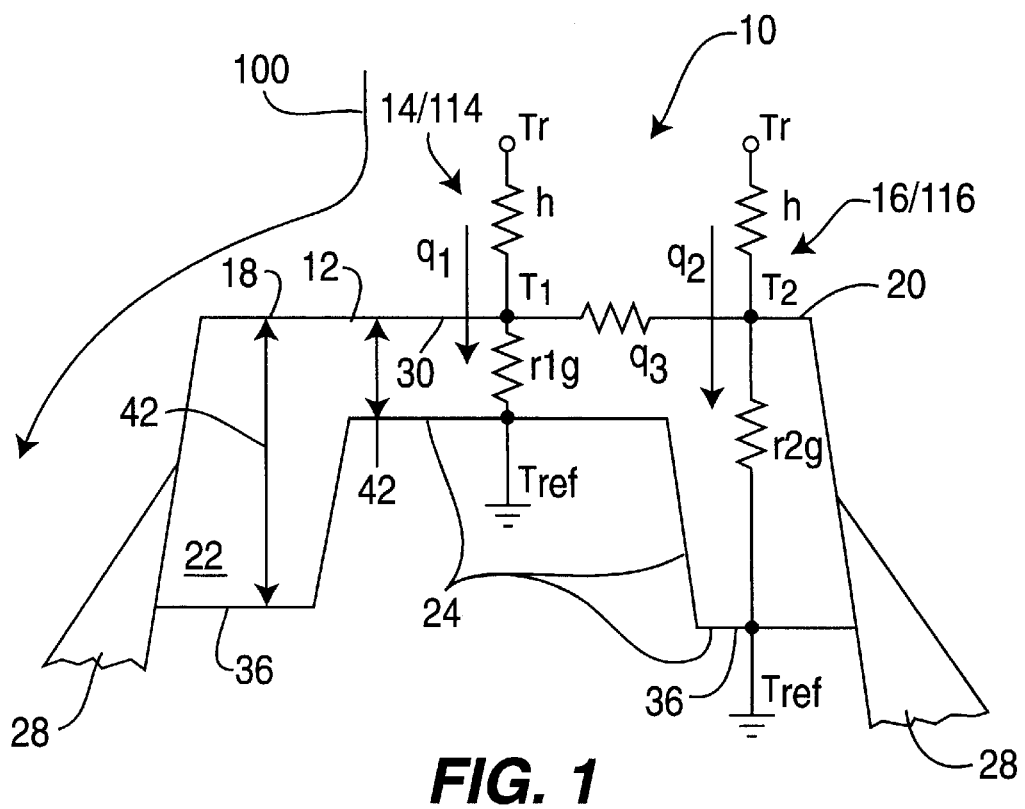
FIG. 1 depicts electrical equivalent circuits of the rapid response thin film sensor and the edge view of the physical outline of the mounted thin film sensor used as part of a preferred embodiment of the present invention.

In FIG. 2A, an equivalent circuit diagram of a preferred embodiment of an h-q-T sensor assembly 10 for determining heat transfer coefficients (h) and recovery temperature ($T_r$) is shown. As seen in FIG. 1, the h-q-T sensor assembly 10 comprises at least a substrate 22 forming a front or upper surface 20, and a first 14 and second 16 temperature indicators that are integrated and mounted onto the same substrate 22. The first temperature indicator 14 is co-located with a heat flux indicator 114 for indicating a heat flux, $q_1$ 17, on the front surface 20. The second temperature indicator 16 is spaced apart from the first temperature indicator 14. The temperature indicators 14 and 16 are preferably micro-indicators that use resistive temperature indicators to measure temperature. The $T_1$ surface-mounted indicator 14 is co-located with a thin film thermopile heat flux indicator 114 exposed to the common mass efflux environment across the front surface 20.

The substrate 22 comprises a material suitable for enduring severe environmental conditions. Maximum heat flux is limited only by the temperature properties of the substrate and the materials of the thin film sensor components 12 incorporated in a layer upon the substrate 22 of the h-q-T sensor assembly 10. Suitable thin film sensor components 12 and substrate 22 compositions include any thermally conductive compositions that allow rapid response measurement of heat flux. The composition of the substrate 22 may include ceramic materials such as silicon nitride, carbons, such as diamond, aluminum nitride, silicon carbide, copper, and/or other materials suitable as a substrate 22 on which to place at least two thin film temperature indicators, such as an RTS 14, 16, and at least one heat flux indicator, such as a thermopile 114, and as a conductive path for h-q-T sensor use, with the material composition being determinable by those skilled in the art. Generally the h-q-T sensor assembly 10 further comprises a front surface 20 low emissivity (dark) protective over-covering film 18, such as aluminum oxide or other known thin-film protective materials with the selection of the type of low emissivity protective over-covering 18 being determinable by those skilled in the art; although the use of a hard-surface in a protective over-covering 18 is not demanded to enable the method of the h-q-T sensor assembly to work. However, the use of a dark low emissivity surface coating aids in the measurement of radiation components of the heat transfer coefficient. The h-q-T assembly 10 comprises a total thickness 30 suitable for determining operational measurements. Preferably, the h-q-T assembly 10 has a thickness 30 (that includes all layers) of from about 1.5 to about 2.5$\mu$, preferably from about 1.7 to about 2.3 $\mu$, and more preferably from about 1.9 to about 2.1$\mu$. With a thin h-q-T assembly 10 thickness 30 of approximately 2$\mu$, the h-q-T assembly 10 does not disturb the gas flow from the rocket plume. The protective over-covering 18 extending over the entire front surface 20 of h-q-T assembly 10 preferably has a thickness of from about 0.1 to about 0.5 $\mu$, more preferably from about 0.2 to about 0.4$\mu$, still more preferably from about 0.25 to about 0.35$\mu$, and most preferably from about 0.28 to about 0.32$\mu$. Electrical connections, shown ending in protrusions 36 at the back or lower surface 24, 32 through the substrate 22 are made by feed-through pins 37, or wrap-around circuit traces (not separately shown), in which the pins 37 are held in contact with the RTS 14, 16, conductors, and the heat flux indicator 114 under controlled tension. At least two RTSs 14, 16 and one heat indicator 114 provide a quasi-linear indication of the front surface 20 temperature, $T_{wall}$, of the h-q-T sensor assembly 10. The heat flux indicator 114 and the RTS 14 are co-located while the RTS 16 is placed as physically close to RTS 14 as practical on the front surface 20 of the h-q-T sensor assembly 10. Protrusions 36 from the through pins 37 to instrumentation project from the back surface 24 of the h-q-T sensor assembly 10. Good contact between the perimeter of the substrate 22 and the mounting 28 permit thermal grounding and proper functioning of the h-q-T sensor assembly 10. Permanent mountings 28 may require the use of high temperature adhesives, such as ceramic cement.

Although the first and second temperature indicators 14 and 16 may be formed upon the same substrate 22, as shown in FIG. 1, the thermal resistance $r_{1g}$ 13 of the substrate 22 along the connecting path from temperature indicator 14 (nominally an RTS) and heat flux indicator 114 (nominally a thin film thermopile) to the reference surface 24 (at which $T_{ref\ 1}$ is maintained or measured) is different from the thermal resistance, $r_{2g}$ 15, of the substrate 22 along the path from the second temperature indicator 16 to the reference surface 24 at which $T_{ref\ 2}$ is maintained or measured. Thermal resistance, $r_{1g}$ 13 and $r_{2g}$ 15, may be varied by any suitable method known in the art, such as varying the thickness of the substrate 22 or the composition of the substrate 22 at appropriate locations, or both.

On the opposite side of the h-q-T sensor assembly 10 from the front surface 20, i.e., the back, or reference, surface 24 at which $T_{ref\ 1}$ and $T_{ref\ 2}$ are maintained or measured, a reference temperature ($T_{ref}$)≈$T_{ref\ 1}$≈$T_{ref\ 2}$ is obtained from a back, or reference, surface 24 that may be actively cooled. The cooled surface 24 may be aided with an augmented active cooling system, i.e., a heat sink. Copper inlet ducts and/or coaxial outlet ducts may be used. The active cooled regions maintain a constant reference or provide a measured "ground" temperature, $T_{ref}$. Water or other fluids may be used to provide the heat sink cooling of the reference (back) surface 24, with the water used as a liquid or flashed to steam as the active coolant. The reference temperature ($T_{ref}$) may be selected from either of two usage methods: working from a constant for a cooled reference (back) surface 24, or from an uncooled reference (back) surface 24 that is exposed only for a very short time so that the temperature rise within the substrate 22 is insignificant, or working from a measured value by use of thermocouples (not separately shown) on the cooled reference (back) surface 24 of the h-q-T sensor assembly 10. Two separate conductive paths, related to the first temperature indicator 14 and second temperature indicator 16, are used to access the reference (back) surface 24 which is used as the ground node in the equivalent electrical circuit of FIG. 2A. The first temperature indicator 14, co-located heat flux indicator 114, and second temperature indicator 16 are generally placed close together on the front surface 20 to provide the best position accuracy for the measurement in the desired flow condition. The front surface 20 of the h-q-T sensor assembly 10 may include any suitable size and/or diameter useful for a given use, with front surface 20 diameters typically ranging from about ¼ inch to about ½ inch, or about ¼ inch to about ½ inch. The maximum separation distance between the first and second temperature indicators 14 and 16 is generally dependent on the size of the front surface 20 of the h-q-T sensor assembly 10. However, as the first and second temperature indicators 14 and 16 are placed closer together, greater accuracy is obtained in the measured and calculated values. Preferably the distance between the first and second temperature indicators 14 and 16 is from about ½ inch or less, more preferably from about ¼ inch to about ½ inch, and most preferably from about 1/16 inch to about ¼ inch.

Measured Values

In the preferred embodiment of the present invention, the h-q-T sensor assembly 10 further comprises two RTS's 14, 16 combined in a single thin film assembly 10. As flow 100 from a severe environment source 50 impinges on the front surface 20 of h-q-T sensor assembly 10, RTS's 14, 16 measure two discrete temperatures, with wall temperature, $T_1$, measured at the first RTS 14 and wall temperature, $T_2$, measured at the second RTS 16. $T_1$ is measured as a surface temperature at the center of the front surface 20, in degrees Rankine (°R). $T_2$ is measured as a surface temperature at the perimeter of the front surface 20, in °R. In addition to the wall temperatures $T_1$ and $T_2$, a reference temperature ($T_{ref}$) may be measured using a thermocouple at the cooled back surface 24. The heat flux indicator 114, comprising a thermopile, measures the heat flux, $q_1$ 17, at the center of the front surface 20 of the thin film sensor 12. The directly measured $q_1$ 17 is generally in units of BTUs per second (BTU/sec). Other measured values include the value of $r_{2g}$ 15, which is the conductive path resistance from the second RTS 16 to the reference (back) surface 24 where $T_{ref\ 2}$ is maintained or measured. The value of $r_{2g}$ 15 is determined from calibration of the second RTS 16. With the measured values of $T_1$, $T_2$, $T_{ref}$, $r_{2g}$ 15, and $q_1$ 17 obtained from the h-q-T sensor assembly 10, calculation of the value of the heat transfer coefficient (h) and the recovery temperature ($T_r$) is possible.

Assumptions About Measured Values

Generally, the temperature at the center of the front surface 20 is less than the temperature at the perimeter of the front surface 20. The front surface 20 temperature at the location where $T_1$ is measured is less than the front surface 20 temperature where $T_2$ is measured ($T_2 > T_1$) and the conductive resistance of the substrate, $r_{1g}$ 13, associated with RTS 14 that measures $T_1$ is also less than the conductive resistance of the substrate, $r_{2g}$ 15 associated with RTS 16 that is used to measure $T_2$ ($r_{1g}$ 13 < $r_{2g}$ 15). Accordingly, the heat flux at $q_1$ 17 is greater than the heat flux at $q_2$ 19 ($q_1 > q_2$) as long as one can assume across the front surface 20 $T_r$ is the same at RTS 14 and RTS 16 (and that temperature changes due to heat capacitance effects do not exist within the substrates), with $T_2$ minus $T_1$ approaching zero as the surface area of the front surface 20 of the h-q-T sensor assembly 10 decreases. Assuming the value of a negligible heat flux along front surface 20 between RST 14 and RST 16, i.e., $q_3 \cong 0$; if $r_{1g}$ 13=0, then $T_1 = T_{ref}$ and $q_1$ is large. If $r_{2g}$ 15=∞, then $T_2 = T_r$ and $q_2$ 19→0. As such, then $T_r \cong T_2$ (measured) and $h = (T_r - T_{ref})/q_{1=(T2-Tref)}/q_1$, where $q_1$ 17 and $T_{ref}$ are measured. However given that $r_{1g}$ 13>0 and $r_{2g}$ 15<∞, and $q_3 \cong 0$ (assumed):

$$h = \frac{1 - \frac{T_2}{r_{2g}}}{T_2 - T_1} \text{ and,} \quad (I)$$

$$T_r = \frac{q_1(T_2 - T_1)}{\left(1 - \frac{T_2}{r_{2g}}\right)} + T_1 \text{ or,} \quad (II)$$

$$T_r = \frac{q_1}{h} + T_1 \quad (III)$$

The h-q-T sensor assembly 10 establishes a differential surface temperature, operating on the premise that universally the front surface 20 temperature ($T_{wall}$) must lie at or between the highest value and lowest value of the front surface 20. The highest value of the adiabatic front surface 20 temperature occurs at a heat flux (q) near zero. Establishing the lowest temperature of the front surface 20 depends upon an arbitrarily high value for q. The highest value for q is established using a highly conductive path to the reference or ground temperature ($T_{ref}$), and can be further augmented by using active cooling at the reference node, such as a heat sink. The $T_{ref}$ is kept as low as feasible, to provide a high value of heat flux, and is set either as a constant or an accurately measured value to establish the values needed to derive h and $T_r$. Ideally, the adiabatic $T_{wall}$ is derived from a zero heat flux path to ground, i.e., an infinite conductive resistance to ground. Conversely, the lowest temperature, $T_1$, of the front surface 20, ideally has a zero conductive resistance $r_{1g}$ 13 to ground and thus is equal to the $T_{ref}$. This is accomplished by requiring $q_1$ 17 to be ∞. In reality, these extremes cannot be met. However, through appropriate arrangements of the physical elements of the thin film sensor components 12 and geometry of the h-q-T sensor assembly 10, sufficient temperature differential is established to derive values for h and $T_r$ that are representative of the condition of the flow at the sensor measurement position and orientation.

The heat transfer coefficient (h) and recovery temperature ($T_r$) are each assumed to maintain the same value across the front surface 20. The presence of melting, sublimation cooling, or erosion at the front surface 20 face (e.g., blowing some cooling air in the boundary layer) are assumed to be non-existent. The effects of heat capacitance within the substrates is assumed to be insignificant, i.e., the Biot number is <<1. Variables $q_1$, $T_1$, $T_2$, $r_{2g}$ 15, and $T_{ref}$ are measured while $r_{1g}$ 13 and $q_2$ 19 are unknown but not needed. As the value of $T_2-T_1$ is small, the value of $q_3$ 21 may be assumed as zero. The h-q-T sensor assembly 10 can be designed to function for steady state and transient conditions as long as the Biot number relationship and thermal capacitance effects are accounted for in the measurement process, i.e., measuring $T_{ref}$. The h-q-T sensor assembly 10 measures $q_1$ 17, $T_1$, and $T_2$, while $r_{2g}$ 15 is determined during the calibration of RTS 16. The heat capacity of the h-q-T sensor assembly 10 substrate 22 limits the temperature change rates at the RTS's 14, 16 without any performance degradation of the thin film sensor components 12.

The unknowns of h and $T_r$ are determined by first calculating the value for the heat transfer coefficient (h), and then calculating the recovery temperature ($T_r$). The stagnation heat transfer coefficient or film coefficient (h) is calculated in BTU per inches squared per seconds per degrees Rankine (BTU/in²/sec/° R). Stagnation point recovery temperature ($T_r$) is calculated in ° R. The value of $r_{2g}$ 15 is established by using calibration methods or measuring $q_2$ 19. As the surface temperature ($T_1$) and heat flux ($q_1$ 17) are measured, the heat transfer coefficient (h) and $r_{1g}$ 13 are determined, $T_r=q(h+r_{1g})$; and the value for heat transfer coefficient, or $h=(T_r-T_1)/q$, is calibrated with measurements of h against known standards to develop a correlation of true film coefficient. Eqns. I and III are used to derive h and $T_r$ from the measured values of $q_1$ 17, $T_1$, $T_2$, and the value of $r_{2g}$ 15 obtained from calibration of RST 16 or by measuring $q_2$ 19. The equations (I57) and (III) above indicate how measurements of $q_1$, $T_1$ and the conductive path resistance (r) are combined to determine the heat transfer coefficient (h) and the recovery ($T_r$). The thin h-q-T sensor assembly 10 may provide a high temperature sub-millisecond response in measuring the front surface 20 or wall temperature ($T_{wall}$) and the heat flux, $q_1$ 17, to derive the stagnation point heat transfer coefficient (h) and ultimately the recovery temperature ($T_r$) conditions by traversing a severe environment rocket plume flowfield. This provides an accurate measure of energy release during the combustion processes by direct and actual measurement of the total energy release. Accordingly, highly-resolved transient energy release of new energetic propellants and warhead explosives may be measured. Additionally, the h-q-T sensor assembly 10 is applicable for developing and characterizing new high efficiency energetic mixes. Other uses include insensitive munitions (IM) tests and bomb damage assessment experiments. The fast response capability of the thin film sensor components 12 allows a rapid sweep or traverse of the h-q-T sensor assembly 10 across the severe environment of the rocket plume, limiting exposure of the thin film sensor components 12, and ensuring that the thin film sensor components 12 are not destroyed and may be re-used. Data provided using the thin film sensor components 12 of the h-q-T sensor assembly 10 generate an upper-bound measure of the heat transfer coefficient (h), i.e., that which occurs without ablative cooling processes, such as melting and erosion.

Figure 5:
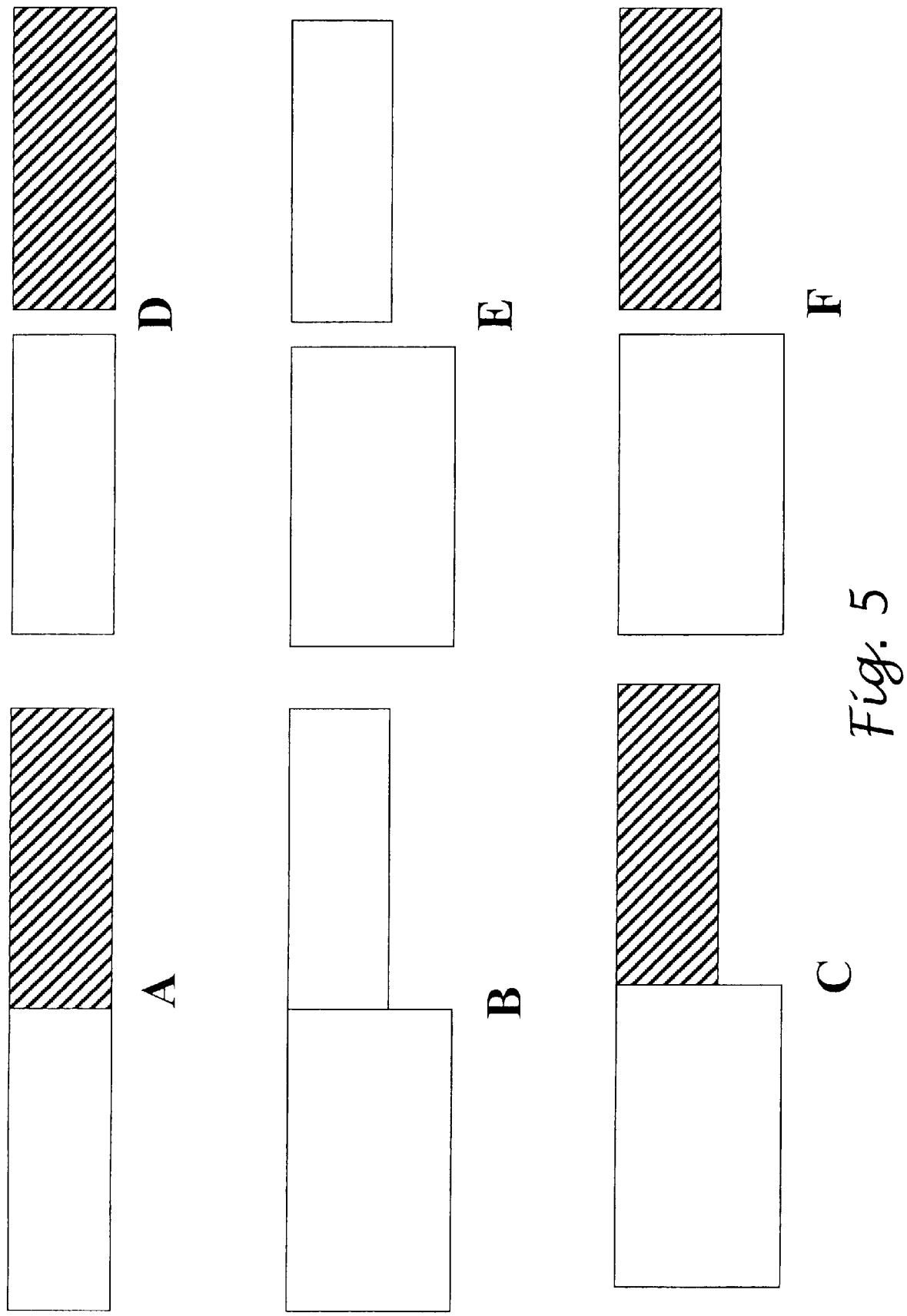
FIG. 5 illustrates edge views of some of the possible combinations in which two separate substrates are used for a preferred embodiment of the present invention.

FIG. 5 provides edge views of various alternative substrate structures that may be used if a single first substrate is provided for measuring $T_1$ and $q_1$ and a single second substrate is provided for measuring $T_2$. The front (upper) 20 and back (lower) 24 surfaces of FIG. 5A have been so designated for aiding in correlating to FIG. 1. Referring to FIG. 5, diagram A depicts separate abutted substrates, each of the same thickness, but constructed of materials having different thermal resistances while diagram D depicts the same arrangement as A for physically separated substrates. Diagram B shows physically abutted substrates differing only in thickness, while Diagram E depicts the same arrangement as B for physically separated substrates. Diagram C depicts abutted substrates of different thicknesses constructed of materials having different thermal resistances while Diagram F depicts the same arrangement as C for physically separated substrates. Thin film sensor components may be manufactured by known techniques in the art. For example, the conducting and insulating patterns of the thin film sensor components 12 may be applied by known sputtering processes.

Figure 3:
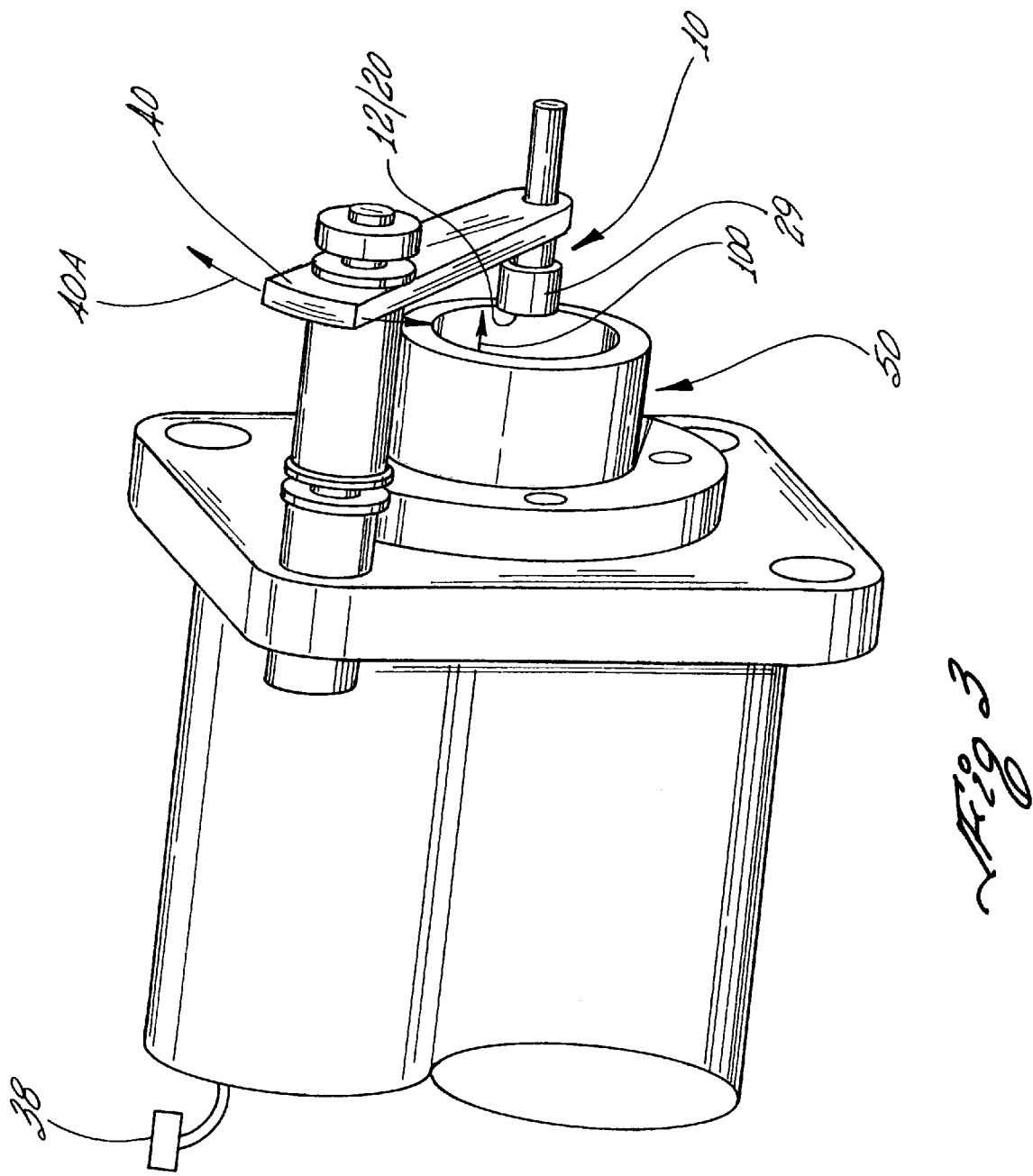
FIG. 3 illustrates a device for positioning a preferred embodiment of the present invention to determine a heat transfer coefficient; and, FIG. 4 illustrates the probe that is mounted on the arm as shown in FIG. 3.

FIG. 3 illustrates a preferred method for determining the heat transfer coefficient with the present invention. FIG. 3 shows a processor 38, applicable to the embodiment of FIG. 1, connected to the first and second temperature indicators 14 and 16 and heat flux indicator 114 for real time calculations of the heat transfer coefficient (h) and recovery temperature ($T_r$). The processor 38 is capable of determining the heat transfer coefficient and recovery temperature from the temperature and heat flux measurements of the first and second temperature indicators 14 and 16 and heat flux indicator 114. Preferably, the processor 38 comprises a microprocessor. Calculation of the heat transfer coefficient within the processor 38 is computed as a value of $$\frac{1-\frac{T_2}{r_{2g}}}{T_2-T_1}$$

Calculation of the recovery temperature within the processor 38 is computed as a value of $$\frac{q_1}{h}+T_1$$

As seen in FIG. 3, the h-q-T sensor assembly 10 may further comprise a probe 29 and a means, such as a rotating or oscillating mechanism, for intermittent alignment 40 of the front surface 20 with a source establishing a severe environment 50. The intermittent alignment of the front surface 20 may last for any suitable period of time that provides heat flux and temperature measurements, while protecting the thin film sensor components 12 from damage. The amount of time that the h-q-T sensor assembly 10 is extended into the flow 100 establishing a severe environment is determined from the corrosive effects of the gases on the thin film sensor components 12, the maximum temperature of the gases, and the time required by the thin film sensor components 12 to obtain surface temperature and heat flux data. The thin film sensor components 12 may respond rapidly to changing heat flux, nominally in <10 $\mu$sec. Within a severe environment the alignment arm 40 intermittently exposes the front surface 20 to the severe environment source 50 for less than one second, preferably from about 0.001 seconds to about 0.5 seconds, more preferably from about 0.01 seconds to about 0.1 seconds, and most preferably from about 0.01 to about 0.05 seconds. The h-q-T sensor assembly 10 may be placed within a severe environment in a manner that limits the exposure of the thin film sensor components 12 to the corrosive affects of the flow 100, either through the type and/or amount of heat, preferably with thin film sensor components 12 cooling being unnecessary. The position of the front surface 20 affects the sweep action relationship to flow direction and boundary layer flows. The thin film sensor components 12 obtain measurements at an extremely rapid rate, allowing a high speed sweep of the h-q-T sensor assembly 10 across a flow 100 from a severe environment source 50, such as a rocket plume. However, the sweep velocity remains significantly slower than the flow 100 from the severe environment source 50, allowing the sweep rate to be disregarded in the determination of h and $T_r$. As such, the manner of exposure of the h-q-T sensor assembly 10 to the flow 100 from the severe environment source 50 is determinable by those skilled in the art, with the h-q-T sensor assembly 10 preferably swept rapidly across the flow 100 to limit exposure of thin film sensor components 12. Thin film sensor components' 12 sensitivity due to temperature drop in the direction of the flow 100 is much less than ±1° C. and the connection resistance effects are minimal as the thin film sensor components 12 act as a low impedance voltage source.

Figure 4:
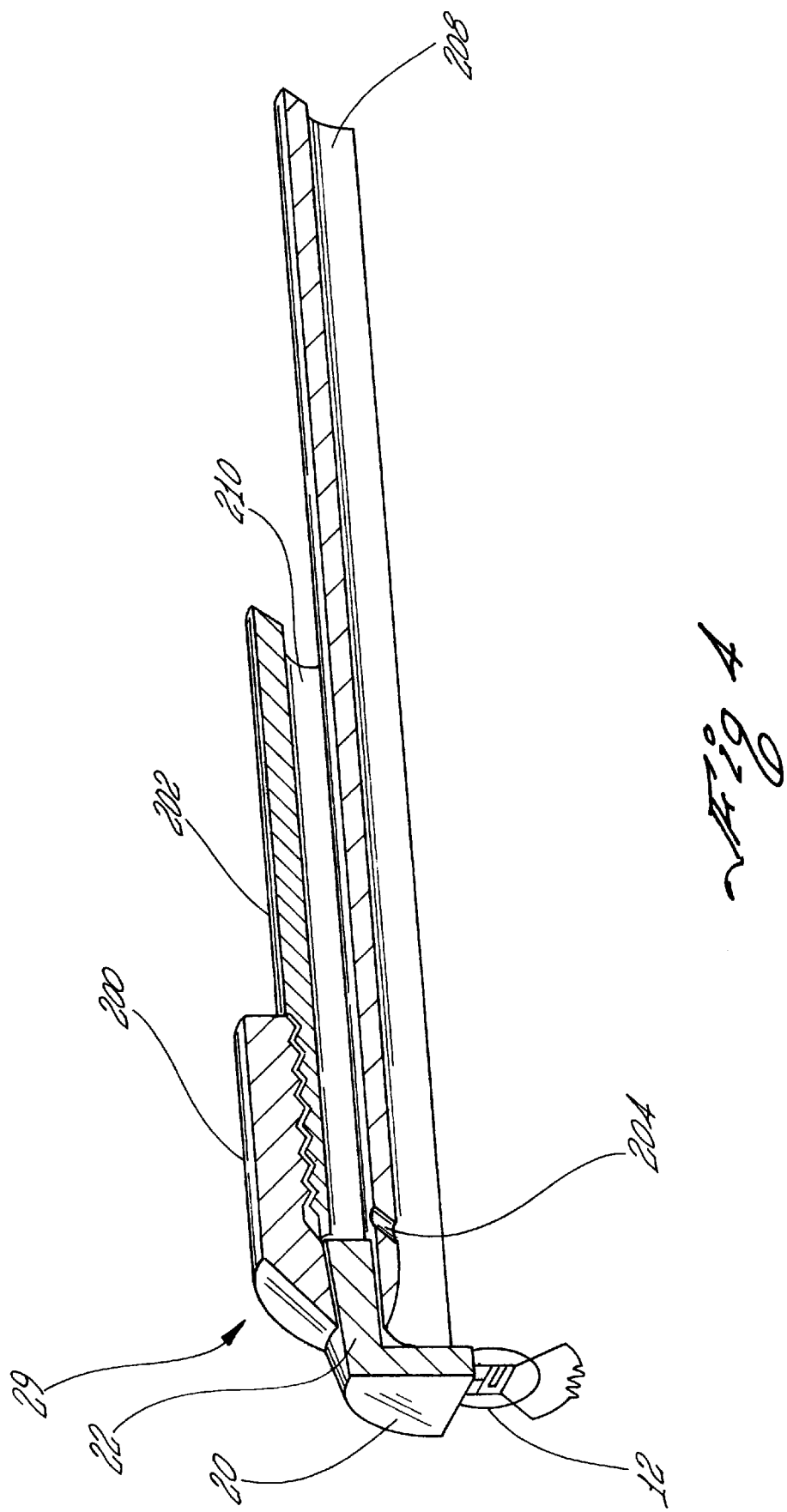

FIG. 4 illustrates the probe 29 of the h-q-T sensor assembly 10 shown in FIG. 3. The thin film sensor components 12 and substrate 22 are attached to the end, connected by a TZM collar nut 200 on a stainless steel body 202. Along the probe 29 is a copper coolant inlet 208 and an h-q-T sensor assembly 10. The Cu coolant inlet 208 provides ducting for the flow of coolant into the reference (back) surface 24, while the thin film sensor components 12 generate signals in response to heat flux and wall temperatures at the sensor front surface 20. Coolant water enters the probe 29 at an $H_2O$ inlet 208 that is at the opposite end of the probe 29 from the thin film sensor components 12. Once the water has functioned as a heat sink for the h-q-T sensor assembly 10, the water/vapor enters a cross-duct 204 and then exits the probe 29 from a $H_2O$ coaxial outlet duct 210.

Thermopile and thermocouple metals used for heat flux and/or temperature measurement may include combinations of copper (Cu), nickel (Ni), chromium (Cr), platinum (Pt), rhodium (Rh), rhenium (Re), tungsten (W) and/or other similarly known metals. Preferably, a variety of different metals are used within the same thin film sensor. Most preferably, copper/nickel, nickel-chromium/nickel, nickel-chromium/platinum, tungsten-rhenium and/or platinum/platinum-rhodium metal combinations are used. The RTS 14, 16 comprises any suitable metal, preferably platinum. Additionally, suitable ceramic materials may be used for the substrate 22.

The preferred source impedance of the present invention ranges from about 50 to about 100Ω, depending on the type of metals used. Preferred heat flux indicator 114 sensitivity ($\mu V/W/cm^2$) ranges from about 2 to about 30, with resistance at 25° C. preferably ranging from about 150±50Ω, and sensitivity (Ω/° C.) preferably being from 0.25–0.35. The maximum operating temperature of the thin film sensor components 12 is limited by the thin film's composition and lead insulation which can be customized for each application.

A typical temperature profile across the front surface 20 indicates variation of temperature proportional to the geometric shape of the front surface 20. For example, the wall temperature ($T_{wall}$) at the center area of the front surface 20 may range from about 1680° R to about 1830° R, while the outer perimeter area of the front surface 20 ranges from about 1970° R or greater. The temperature difference is caused by thicknesses varying between the center of the substrate 22 and areas along the perimeter of the front surface 20. This thickness differential causes a different conductive path resistance ($r_{1g}$ 13<$r_{2g}$ 15) to the reference (back) surface 24. The geometry change imposes a change of conductive path heat flux that is associated with each RTS 14, 16, and the corresponding difference in the surface temperature, i.e., $T_2>T_1$. By using appropriate heat transfer circuit analysis methods and calibrations of the conductive path characteristics, the values for heat transfer coefficients (h) and the recovery temperature ($T_r$) are properly determined.

The rapid response h-q-T sensor is particularly useful in fire science applications. Examples of the application of the present invention non-exclusively include bomb blast effects, jet vanes, turbine blades, nozzles, RV nosetip erosion, seeker domes, jets, rockets, bombs, insensitive munitions, VLS launcher systems, thrust vector control systems development, power plants, combustion, volcano/lava flows, launcher/canister analysis, rocket plume measurement, energy assessments, improved and broadened understanding of flames, plumes, blasts, energetic heat release phenomena, validating numerical simulations, anchoring simulated designs with experimental data, developing a thermal condition data base, rocket motor, nozzle, combustion chamber design and development process, high speed aerodynamics, supersonic combustion. boiling heat transfer, flame dynamics, turbine blade cooling, heat transfer in boundary layers and shocks, thermal property measurement, mass flow measurement, and/or blood perfusion measurement.

Additional temperature indicators beyond the first and second temperature indicators 14 and 16 may be incorporated as additions to the thin film sensor components 12, giving a more accurate measurement of heat transfer coefficient. However, any added temperature or heat flux indicators generally provide incremental accuracy. Use of more than one heat flux indicator may be dictated by design choice, and physical limitations of placing the additional heat flux indicators on the front surface 20, with the proper use of the second or more heat flux indicators determinable by those skilled in the art.

In operation, the h-q-T sensor assembly 10 establishes a $T_{ref}$ at the reference (back) surface 24. In one application, an h-q-T sensor assembly 10 mounted on a rotating arm 40 is swept rapidly across a rocket plume near the exit plane of the nozzle with the front surface 20 of the h-q-T sensor assembly 10 maintained perpendicular to the longitudinal axis of the rocket plume. The use of thin film technology enables a rapid response such that a rapid sweep across the plume generates sufficient data without destroying the thin film sensor components 12.

EXAMPLE 1

Probe for Solid Rocket Plume Measurements

An h-q-T sensor assembly 10 was tested to measure stagnation point recovery temperature and stagnation heat transfer coefficient of rocket motor plumes. The h-q-T sensor assembly 10 provided accurate measurements of energy released during combustion.

The temperature 14, 16 and heat flux 114 indicators measured heat flux and temperature simultaneously, and responded with heat flux measurements in <10 $\mu$sec. The h-q-T sensor assembly 10 further had a dynamic range >40 dB, and withstood temperatures up to 800° C. The h-q-T sensor assembly 10 was shown to be thermally and aerodynamically non-intrusive, while measuring radiative, convective and conductive heat flux.

The foregoing summary, description, examples, and drawings of the invention are not intended to be limiting, but are only exemplary of the inventive features that are defined in the claims.

What is claimed is:

1. A rapid response thin film sensor assembly, having a front surface of less than one square inch and a back surface maintained during operation at a low temperature with respect to said front surface, at least one layer, and a thickness of less than 5$\mu$, for obtaining within a severe environment at least one measure for each of two values of temperature, $T_1$ and $T_2$, and at least one measure for heat flux, $q_1$, said measures obtained in less than a millisecond, comprising:

a single substrate, having upper and lower surfaces and at least first and second parts, each said upper and lower surface having a center and a perimeter, a pre-specified first thermal resistance, $r_{1g}$, inherent as a characteristic of said first part of said substrate, a pre-specified second thermal resistance, $r_{2g}$, inherent as a characteristic of said second part of said substrate, said substrate having a thickness of less than $2\mu$ wherein $r_{2g} \gg r_{1g}$;

at least a first temperature indicator affixed in said center of said upper surface of said single substrate for measuring a first temperature, $T_1$;

at least a second temperature indicator affixed near said perimeter of said upper surface of said single substrate at a pre-specified distance on said single substrate from said first temperature indicator for measuring a second temperature, $T_2$, wherein heat flux between said first and second temperature indicators along said front surface is negligible;

at least one heat flux indicator for measuring $q_1$ through said front surface and across said first thermal resistance, $r_{1g}$; and a reference area incorporated in said back surface, said reference area in operable communication with said first and second temperature indicators and said at least one heat flux indicator, wherein said reference area is maintained at a reference temperature, $T_{ref} \ll T_2 < T_1$, and in operable communication with said at least one heat flux indicator and said first and second temperature indicators, and wherein use of said thin film sensor permits the further derivation of a heat transfer coefficient (h) and a recovery temperature ($T_r$) within an environment that may include temperatures above 800° C. such as may exist in an exhaust plume from a solid rocket motor.

2. The thin film sensor of claim 1 in which said reference area incorporates at least one thermocouple fabricated from metal selected from the group consisting of: copper, nickel, chromium, platinum, tungsten, rhenium, rhodium, and combinations thereof, for measuring a reference temperature, $T_{ref}$, and said back surface is cooled via a fluid selected from the group consisting of air, water, flashed steam, and a non-volatile fluid.

3. The thin film sensor of claim 1 in which said operable communication through said single substrate is accomplished via means selected from the group consisting of:

feed-through pins held in contact with said temperature indicators and said heat flux indicators via controlled tension; and wrap-around circuit traces.

4. The thin film sensor of claim 1 in which said at least one heat flux indicator comprises a thermopile with electrical sensitivity in the range of 2–30 $\mu$V/W/cm$^2$, resistance in the range of 100–200$\Omega$, and thermal sensitivity of 0.25–0.35$\Omega$/° C., and is fabricated from metal combinations selected from the group consisting of: copper/nickel, nickel-chromium/ nickel, nickel-chromium/platinum, tungsten-rhenium, platinum/platinum-rhodium, and combinations thereof.

5. The thin film sensor of claim 1 in which said single substrate may be constructed from material selected from the group consisting of: silicon nitride, carbon, diamond, aluminum nitride, silicon carbide, copper, and combinations thereof.

6. The thin film sensor of claim 1 further comprising a low emissivity protective layer of less than $1.0\mu$ thickness on said front surface.

7. The thin film sensor of claim 6 in which said protective layer is less than $0.5\mu$ thick and is selected from the group consisting of: aluminum oxide ($Al_2O_3$), silicon oxide($SiO_x$), a combination of aluminum oxide ($Al_2O_3$) and silicon oxide ($SiO_x$), and high silicon glass.

8. The thin film sensor of claim 6 in which said protective layer is between $0.28\mu$ and $0.32\mu$ thick, and is selected from the group consisting of: aluminum oxide ($Al_2O_3$), silicon oxide ($SiO_x$), a combination of aluminum oxide ($Al_2O_3$) and silicon oxide ($SiO_x$), and high silicon glass.

9. The thin film sensor of claim 1 in which said temperature indicators are resistance temperature sensors (RTS).

10. The thin film sensor of claim 1 having a thickness of less than $2.5\mu$ and having said front surface area less than 0.2 square inches.

11. The thin film sensor of claim 1 having a thickness between $1.9\mu$ and $2.1\mu$ and having said front surface area between 0.05 square inches and 0.2 square inches.

12. A rapid response thin film sensor assembly, having a upper surface of less than one square inch and a lower surface maintained during operation at a low temperature with respect to said upper surface, at least one layer, and a thickness of less than $5\mu$, for obtaining within a severe environment at least one measure for each of two values of temperature, $T_1$ and $T_2$, and at least one measure for heat flux, $q_1$, said measures obtained in less than a millisecond, comprising:

first and second substrates each having upper and lower surfaces, said first substrate of said thin film sensor having a first pre-specified thermal resistance, $r_{1g}$, inherent as a characteristic of said first substrate, and incorporating in said first substrate's upper surface at least one heat flux indicator and a first temperature indicator and said second substrate, having a second pre-specified thermal resistance, $r_{2g}$, inherent as a characteristic of said second substrate, incorporating in said second substrate's upper surface a second temperature indicator, wherein said second substrate; may abut said first substrate such that said upper surface of said first substrate lies in the same plane as said upper surface of said second substrate, wherein each of said first and second substrates has a thickness of less than $2\mu$;

wherein $r_{2g} \gg r_{1g}$;

wherein said first temperature indicator measures said first temperature, $T_1$ and said second temperature indicator measures said second temperature, $T_2$;

wherein heat flux between said first and second temperature indicators is negligible;

wherein said at least one heat flux indicator measures said heat flux, $q_1$, through said upper surface of said first substrate and across said first thermal resistance, $r_{1g}$;

a reference area incorporated in at least one of said lower surfaces of said first and second substrates, said reference area in operable communication with said first and second temperature indicators and said at least one heat flux indicator, wherein said reference area is maintained at a reference temperature, $T_{ref} \ll T_2 < T_1$, and wherein use of said thin film sensor permits the further derivation of a heat transfer coefficient (h) and a recovery temperature ($T_r$) within an environment that may include temperatures above 800° C. such as may exist in an exhaust plume from a solid rocket motor.

13. The thin film sensor of claim 12 in which said operable communication through said first and second substrates is accomplished via means selected from the group consisting of:
   feed-through pins held in contact with said temperature indicators and said heat flux indicators via controlled tension; and
   wrap-around circuit traces.

14. The thin film sensor of claim 12 in which said first and second substrates may be constructed from material selected from the group consisting of: silicon nitride, carbon, diamond, aluminum nitride, silicon carbide, copper, stainless steel, and combinations thereof.

15. The thin film sensor assembly of claim 12 in which said at least one reference area incorporates at least one thermocouple fabricated from metal selected from the group consisting of: copper, nickel, chromium, platinum, tungsten, rhenium, rhodium, and combinations thereof, for measuring a reference temperature, $T_{ref}$, and said back surface is cooled via a fluid selected from the group consisting of air, water, flashed steam, and a non-volatile fluid.

16. The thin film sensor assembly of claim 12 in which said at least one heat flux indicator comprises a thermopile with electrical sensitivity in the range of 2–30 $\mu V/W/cm_2$, resistance in the range of 100–200$\Omega$, and thermal sensitivity of 0.25–0.35$\Omega/°$ C., and is fabricated from metal combinations selected from the group consisting of: copper/nickel, nickel-chromium/nickel, nickel-chromium/platinum, tungsten-rhenium, platinum/platinum-rhodium, and combinations thereof.

17. The thin film sensor assembly of claim 12 further comprising a low emissivity protective layer of less than 1.0$\mu$ thickness on each said upper surface of said first and second substrates.

18. The thin film sensor assembly of claim 17 in which said protective layer is less than 0.5$\mu$ thick and is selected from the group consisting of: aluminum oxide ($Al_2O_3$), silicon oxide ($SiO_x$), a combination of aluminum oxide ($Al_2O_3$) and silicon oxide ($SiO_x$), and high silicon glass.

19. The thin film sensor assembly of claim 17 in which said protective layer is between 0.28$\mu$ and 0.32$\mu$ thick, and is selected from the group consisting of: aluminum oxide ($Al_2O_3$), silicon oxide ($SiO_x$), a combination of aluminum oxide ($Al_2O_3$) and silicon oxide ($SiO_x$), and high silicon glass.

20. The thin film sensor assembly of claim 12 in which said operable communication through said first and second substrates is accomplished via means selected from the group consisting of:
   feed-through pins held in contact with said temperature indicators and said heat flux indicators via controlled tension; and
   wrap-around circuit traces.

21. The thin film sensor assembly of claim 12 in which said temperature indicators are resistance temperature sensors (RTS).

22. The thin film sensor assembly of claim 12 having a thickness of less than 2.5$\mu$ and having said upper surface area less than 0.2 square inches.

23. The thin film sensor assembly of claim 12 having a thickness between 1.9$\mu$ and 2.1$\mu$ and having said upper surface area between 0.05 square inches and 0.2 square inches.

24. A system for determining a heat transfer coefficient (h) and recovery temperature ($T_r$) while taking measurements within a severe environment, comprising:
   a rapid response thin film sensor assembly, having a front surface with a center and a perimeter said front surface being less than one square inch in area, and a back surface maintained during operation at a low temperature with respect to said front surface, at least one layer, the sensor's thickness being less than 5$\mu$, for obtaining at least one measure for each of two values of temperature, $T_1$ and $T_2$, and at least one measure for heat flux, $q_1$ said measures obtained in less than a millisecond, comprising:
      a single substrate, having upper and lower surfaces and at least first and second parts, each said upper and lower surface having a center and a perimeter, a pre-specified first thermal resistance, $r_{1g}$, that can be measured across said first part of said substrate, a pre-specified second thermal resistance, $r_{2g}$, that can be measured across said second part of said substrate, said substrate having a thickness of less than 2$\mu$ wherein $r_{2g} >> r_{1g}$;
   at least a first temperature indicator affixed in said center of said upper surface of said first substrate for measuring a first temperature, $T_1$;
   at least a second temperature indicator affixed near said perimeter of said upper surface of said single substrate at a pre-specified distance on said single substrate from said first temperature indicator for measuring a second temperature, $T_2$,
   wherein heat flux between said first and said at least a second temperature indicators along said front surface is negligible;
      at least one heat flux indicator for measuring $q_1$ through said front surface and across said first thermal resistance, $r_{1g}$;
      a reference area incorporated in said back surface, said reference area in operable communication with said first and said at least a second temperature indicators and said at least one heat flux indicator,
   wherein said reference area is maintained at a reference temperature, $T_{ref} << T_2 < T_1$, and in operable communication with said at least one heat flux indicator and said first and second temperature indicators, and
      at least one processor operably connected to said at least one heat flux indicator and said first and second temperature indicators,
   wherein use of said thin film sensor assembly allows said processor to determine a heat transfer coefficient (h) and a recovery temperature ($T_r$), within an environment that may include temperatures above 800° C. in an exhaust plume from a solid rocket motor.

25. The system of claim 24 further comprising a positioning mechanism that both secures said thin film sensor assembly in a position for taking measurements and provides for transiting said thin film sensor assembly through a severe environment.

26. The system of claim 25 in which said positioning mechanism may transit said thin film sensor assembly into and out of said severe environment in less than one second.

27. The system of claim 24 in which said back surface is actively cooled via circulating a fluid in an active cooling system that may use copper inlet ducts having outlet ducts coaxial therewith,
   wherein, said actively cooled back surface enables said relationship: $T_{ref} << T_2 < T_1$, and wherein, said $T_{ref}$ may be measured via at least one thermocouple operably communicating with said back surface.

28. The system of claim 24 further comprising a low emissivity protective layer of less than 1.0$\mu$ thickness on said front surface.

29. The system of claim 28 in which said protective layer is less than $0.5\mu$ thick, and is selected from the group consisting of: aluminum oxide ($Al_2O_3$), silicon oxide ($SiO_x$), a combination of aluminum oxide ($Al_2O_3$) and silicon oxide ($SiO_x$), and high silicon glass.

30. The system of claim 28 in which said protective layer is between $0.28\mu$ and $0.32\mu$ thick, and is selected from the group consisting of: aluminum oxide ($Al_2O_3$), silicon oxide ($SiO_x$), a combination of aluminum oxide ($Al_2O_3$) and silicon oxide ($SiO_x$), and high silicon glass.

31. The system of claim 24 in which said single substrate may be constructed from material selected from the group consisting of: silicon nitride, carbon, diamond, aluminum nitride, silicon carbide, copper, stainless steel, and combinations thereof.

32. The system of claim 24 whereby said processor first computes said heat transfer coefficient, h, from the relation:

$$h = \frac{1 - \frac{T_2}{r_{2_K}}}{T_2 - T_1}.$$

33. The system of claim 24 whereby said processor further computes said recovery temperature, $T_r$, from the relation:

$$T_r = \frac{q_1}{h + T_1}.$$

34. The system of claim 24 in which said operable communication through said first and second substrates is accomplished via means selected from the group consisting of:
feed-through pins; and
wrap-around circuit traces, and,
wherein said operable connection to said processor from said at least one heat flux indicator and said at least one first and at least one second temperature indicators is via at least one projection from said back surface of said thin film sensor assembly.

35. The system of claim 24 in which said feed-through pins are held in contact with said temperature indicators and said at least one heat flux indicator via controlled tension.

36. The system of claim 24 in which at least one said first and second temperature indicators comprises an RTS.

37. A system incorporating a rapid response thin film sensor assembly, having a front surface of less than one square inch and a back surface maintained during operation at a low temperature with respect to said front surface, at least one layer, and a thickness of less than $5\mu$, for obtaining within a severe environment at least one measure for each of two values of temperature, $T_1$ and $T_2$, and at least one measure for heat flux, $q_1$, said measures obtained in less than a millisecond, comprising:
first and second substrates each having upper and lower surfaces, said first substrate of said thin film sensor having a first pre-specified thermal resistance, $r_{1g}$, inherent as a characteristic of said first substrate, and incorporating in said first substrate's upper surface at least one heat flux indicator and a first temperature indicator and a second pre-specified thermal resistance, $r_{2g}$, inherent as a characteristic of said second substrate, and incorporating in said second substrate's upper surface a second temperature indicator,
wherein said second substrate; may abut said first substrate such that said upper surface of said first substrate lies in the same plane as said upper surface of said second substrate,
wherein each of said first and second substrates has a thickness of less than $2\mu$;
wherein $r_{2g} \gg r_{1g}$;
wherein said first temperature indicator measures said first temperature, $T_1$ and said second temperature indicator measures said second temperature, $T_2$;
wherein heat flux between said first and second temperature indicators is negligible;
wherein said at least one heat flux indicator measures said heat flux, $q_1$, through said upper surface of said first substrate and across said first thermal resistance, $r_{1g}$;
a reference area incorporated in at least one of said lower surfaces of said first and second substrates, said reference area in operable communication with said first and second temperature indicators and said at least one heat flux indicator,
wherein said reference area is maintained at a reference temperature, $T_{ref} \ll T_2 < T_1$, and
wherein use of said thin film sensor permits the further derivation of a heat transfer coefficient (h) and a recovery temperature ($T_r$) within an environment that may include temperatures above 800° C. such as may exist in an exhaust plume from a solid rocket.

38. A method using a thin film sensor assembly for determining, in a severe environment in which ambient temperatures nominally exceed 800° C., at least one value for a heat transfer coefficient, h, and at least one value for a recovery temperature, $T_r$, as derived from:
providing a system using at least one rapid response thin film sensor assembly, having a structure with at least a front and a back surface, at least a first temperature indicator incorporated in a pre-specified first area of said front surface for measuring a temperature, $T_1$, at least a second temperature indicator incorporated in a pre-specified second area of said front surface separated from said pre-specified first area for measuring a temperature, $T_2$, and at from at least one heat flux indicator co-located with said first temperature indicator for measuring at least one value of heat flux, $q_1$;
exposing said system to the severe environment intermittently;
taking at least one temperature measurement, each said measurement taken in less than ten $\mu$seconds, of at least one value for each of said at least two temperature measurements, $T_1$ and $T_2$;
taking at least one heat flux measurement of at least one value for said heat flux, $q_1$, one of at least two nominally available heat flux measurements, $q_1$ and $q_2$, said at least one heat flux measurement being taken across a first specified area having a resistance, $r_{1g}$, one of at least two thermal resistances, $r_{1g}$ and $r_{2g}$, said $r_{2g}$ being a resistance across a second specified area different from said first specified area, where $r_{2g} \gg r_{1g}$, said $r_{1g}$ and $r_{2g}$ being measurable characteristics of said structure of said thin film sensor assembly,
wherein $r_{2g}$ may be determined via a calibration or be derived from measuring a value for said $q_2$;
taking at least one measurement of a maintained reference temperature, $T_{ref}$, from at least one location on said back surface;

wherein $T_{ref} \ll T_2 < T_1$, and
wherein said back surface may be actively cooled to maintain the relationship:
$T_{ref} \ll T_2 < T_1$;
 intermittently passing said thin film sensor assembly into and back out of said severe environment; and
 processing data, from said measurements taken when said thin film sensor assembly is intermittently passed into said severe environment, to determine at least one recovery temperature, $T_r$, and at least one heat flux coefficient, h.

39. The method of claim 38 in which said thin film sensor assembly is exposed to said severe environment for less than 50 milliseconds during any single said intermittent exposure.

* * * * *